(12) United States Patent
Jepsen

(10) Patent No.: US 8,858,992 B2
(45) Date of Patent: Oct. 14, 2014

(54) HIGH DRUG LOAD MESALAZINE SACHET

(75) Inventor: Svenn Klüver Jepsen, Holte (DK)

(73) Assignee: Ferring B.V., Hoofddorp (NL)

( * ) Notice: Subject to any disclaimer, the term of this patent is extended or adjusted under 35 U.S.C. 154(b) by 988 days.

(21) Appl. No.: 10/553,629

(22) PCT Filed: Apr. 23, 2004

(86) PCT No.: PCT/EP2004/004297
§ 371 (c)(1),
(2), (4) Date: Jul. 20, 2006

(87) PCT Pub. No.: WO2004/093884
PCT Pub. Date: Nov. 4, 2004

(65) Prior Publication Data
US 2007/0043004 A1   Feb. 22, 2007

Related U.S. Application Data

(60) Provisional application No. 60/464,649, filed on Apr. 23, 2003.

(30) Foreign Application Priority Data

Apr. 23, 2003 (DK) .................................. 2003 00612
Apr. 23, 2003 (EP) ....................................... 03388023

(51) Int. Cl.
| | | |
|---|---|---|
| *A61K 9/20* | (2006.01) | |
| *A01N 37/36* | (2006.01) | |
| *A61K 9/16* | (2006.01) | |
| *B32B 27/10* | (2006.01) | |
| *A61K 9/50* | (2006.01) | |
| *A61K 31/60* | (2006.01) | |

(52) U.S. Cl.
CPC ............. *A61K 9/1635* (2013.01); *A61K 9/1694* (2013.01); *B32B 27/10* (2013.01); *A61K 9/5042* (2013.01); *A61K 31/60* (2013.01)
USPC .......................................... 424/464; 514/166

(58) Field of Classification Search
CPC ... A61K 9/2054; A61K 31/60; A61K 9/5042; A61K 9/1635; A61K 9/1694
USPC .......................................... 424/464; 514/166
See application file for complete search history.

(56) References Cited

U.S. PATENT DOCUMENTS

| | | |
|---|---|---|
| 3,758,563 A | 9/1973 | Uematsu et al. |
| 4,632,921 A | 12/1986 | Bauer |
| 4,720,473 A | 1/1988 | Welch et al. |
| 4,880,794 A | 11/1989 | Halskov |
| 4,960,765 A | 10/1990 | Halskov |
| 4,980,173 A | 12/1990 | Halskov |
| 5,013,727 A | 5/1991 | Halskov |
| 5,188,841 A | 2/1993 | Simpkin et al. |
| 5,194,464 A * | 3/1993 | Itoh et al. .......................... 524/42 |
| 5,254,347 A | 10/1993 | Samejima et al. |
| 5,316,772 A * | 5/1994 | Jurgens et al. ................. 424/472 |
| 5,472,712 A | 12/1995 | Oshlack et al. |
| 5,482,718 A | 1/1996 | Shah et al. |
| 5,484,605 A | 1/1996 | Scheiffele et al. |
| 5,541,170 A | 7/1996 | Rhodes et al. |
| 5,544,426 A | 8/1996 | Yoshida et al. |
| 6,004,581 A | 12/1999 | Jepsen |
| 6,245,351 B1 | 6/2001 | Nara et al. |
| 6,773,720 B1 | 8/2004 | Villa et al. |
| 6,962,717 B1 | 11/2005 | Huber et al. |
| 7,022,345 B2 | 4/2006 | Valducci |
| 8,282,955 B2 | 10/2012 | Jepsen |
| 8,282,958 B2 | 10/2012 | Jepsen |
| 8,501,226 B2 | 8/2013 | Jepsen |
| 8,697,135 B2 | 4/2014 | Jepsen |
| 2001/0046964 A1 | 11/2001 | Percel et al. |
| 2002/0034541 A1 * | 3/2002 | Valducci ........................ 424/464 |
| 2002/0177579 A1 * | 11/2002 | Augsburger et al. ......... 514/102 |
| 2006/0006258 A1 | 1/2006 | Remon et al. |
| 2013/0022681 A1 | 1/2013 | Hoeg-Moller et al. |

FOREIGN PATENT DOCUMENTS

| | | |
|---|---|---|
| DE | 100 13 030 | 9/2001 |
| EP | 0148811 A1 | 7/1985 |
| EP | 0 540 813 | 5/1993 |
| EP | 1004297 | 5/2000 |
| EP | 1172100 | 1/2002 |
| GB | 2 163 957 | 3/1986 |
| JP | 57-11912 | 1/1982 |
| JP | 57-58631 | 4/1982 |
| JP | 8-26977 | 1/1996 |
| JP | 2001-55322 | 2/2001 |
| JP | 2003-501458 | 1/2003 |
| WO | WO 81/02671 A | 10/1981 |
| WO | WO 91/16042 A1 | 10/1991 |

(Continued)

OTHER PUBLICATIONS

Nakashima et al., "Particle Design and Processing Technology which are Readily Useful," *Chem. Pharm. Bull.*, 46(3), 1998, 3 pages. (Translation Attached).
Ferring Pharmaceuticals: "Pentasa Sachet: Prolonged Release Granules 1 g", Homepage Ferring Pharmaceuticals Online Jan. 19, 2001, pp. 1-2. URL:http://www.ferring.com/site/ferring_com/view.asp?ID=510>.
Nakamura et al., Folia Pharmacol., Jpn. 1994, vol. 104, 303-311, Abstract only.
Percev et al., ed., "NFAY," Farmatsevticheskie I medico-biologicheskie aspekty lekarstv, Kharkov, vol. 2, pp. 360-362, 1999.
Chueshov, "Promyshlennaja technologija lekarstv," vol. 2, pp. 383-392, 1999.
U.S. Appl. No. 13/956,733, filed Aug. 1, 2013, Jepsen.
Klein et al., "Drug Release Characteristics of Different Mesalazine Products Using USP Apparatus 3 to Simulate Passage Through the GI Tract," *Dissolution Technologies*, Article 1, Nov. 2002, http://www.dissolutiontech.com/DTresour/1102art/1102_art1.htm, accessed on Dec. 12, 2010.

(Continued)

*Primary Examiner* — Aradhana Sasan
(74) *Attorney, Agent, or Firm* — Folely & Lardner LLP

(57) ABSTRACT

The present invention is directed to a high drug formulation having desirable properties in terms of ease of manufacture and visual appearance as well as a sachet for the formulation.

8 Claims, No Drawings

(56) References Cited

FOREIGN PATENT DOCUMENTS

| WO | WO 92/11001 | | 7/1992 | | |
|---|---|---|---|---|---|
| WO | WO 92/14452 | | 9/1992 | | |
| WO | WO 97/23199 | * | 7/1997 | ............... | A61K 9/16 |
| WO | WO 97/23199 A1 | | 7/1997 | | |
| WO | WO 98/03161 A1 | | 1/1998 | | |
| WO | WO 98/04321 A1 | | 2/1998 | | |
| WO | WO 98/26767 | | 6/1998 | | |
| WO | WO 99/21536 | | 5/1999 | | |
| WO | WO 00/21525 A2 | | 4/2000 | | |
| WO | WO 00/44353 | | 8/2000 | | |
| WO | WO 00/76481 | * | 12/2000 | ............... | A61K 9/20 |
| WO | WO 01/66094 | | 9/2001 | | |
| WO | WO 03/032952 A | | 4/2003 | | |

OTHER PUBLICATIONS

U.S. Appl. No. 14/133,934, filed Dec. 19, 2013, Jepsen.
French et al., "Evaluation of the Physicochemical Properties and Dissolution Characteristics of Mesalamine: Relevance to Controlled Intestinal Drug Delivery," *Pharmaceutical Research*, vol. 10, No. 9, pp. 1285-1290, 1993.
Gupta et al., "A novel pH- and time-based multi-unit potential colonic drug delivery system," International Journal of Pharmaceutics, vol. 213, pp. 83-91, 2001.
Thommes et al., "Use of kappa-carrageenan as alternative aid to microcrystalline cellulose in extrusion/spheronisation. II. Influence of drug and filler type," European Journal of Pharmaceutics and Biopharmaceutics, vol. 63, No. 1, pp. 68-75, May 1, 2006.
Hagsten et al., "Identifying sources of batch to batch variation in processability," Powder Technology, vol. 183, pp. 213-219, 2008.
International Search Report issued on Jun. 24, 2011 in application No. PCT/EP2010/069733 (corresponding to US 2013/0022681).
International Search Report issued on Mar. 10, 2006 in application No. PCT/EP2004/053537 (corresponding to US 8,282,958).
International Search Report issued on Jul. 2, 2002 in application No. PCT/DK01/00677 (corresponding to 8,282,955).
Office Action issued on Mar. 31, 2004 by the Examiner in U.S. Appl. No. 10/269,055 (US 2003/0138495).
Office Action issued on Sep. 9, 2005 by the Examiner in U.S. Appl. No. 10/269,055 (US 2003/0138495).
Office Action issued on May 17, 2006 by the Examiner in U.S. Appl. No. 10/269,055 (US 2003/0138495).
Office Action issued on Dec. 29, 2006 by the Examiner in U.S. Appl. No. 10/269,055 (US 2003/0138495).
Office Action issued on Sep. 20, 2007 by the Examiner in U.S. Appl. No. 10/269,055 (US 2003/0138495).
Office Action issued on May 28, 2008 by the Examiner in U.S. Appl. No. 10/269,055 (US 2003/0138495).
Office Action issued on Nov. 19, 2008 by the Examiner in U.S. Appl. No. 10/269,055 (US 2003/0138495).
Office Action issued on Jul. 31, 2009 by the Examiner in U.S. Appl. No. 10/269,055 (US 2003/0138495).
Office Action issued on Apr. 19, 2010 by the Examiner in U.S. Appl. No. 10/269,055 (US 2003/0138495).
Office Action issued on Nov. 9, 2010 by the Examiner in U.S. Appl. No. 10/269,055 (US 2003/0138495).
Office Action issued on Jul. 7, 2011 by the Examiner in U.S. Appl. No. 10/269,055 (US 2003/0138495).
Office Action issued on Oct. 3, 2011 by the Examiner in U.S. Appl. No. 10/269,055 (US 2003/0138495).
Office Action issued on Dec. 20, 2011 by the Examiner in U.S. Appl. No. 10/269,055 (US 2003/0138495).
Notice of Allowance issued on Jun. 7, 2012 by the Examiner in U.S. Appl. No. 10/269,055 (US 2003/0138495).
Office Action issued on Jun. 7, 2013 in U.S. Appl. No. 13/606,443 (US 8,697,135).
Notice of Allowance issued on Sep. 27, 2013 in U.S. Appl. No. 13/606,443 (US 8,697,135).
Office Action issued on Jan. 17, 2013 in U.S. Appl. No. 13/516,145 (US 2013/0022681).
Office Action issued on Jul. 30, 2013 in U.S. Appl. No. 13/516,145 (US 2013/0022681).
Notice of Allowance issued on Feb. 19, 2014 in U.S. Appl. No. 13/516,145 (US 2013/0022681).
Office Action issued on Nov. 27, 2009 by the Examiner in U.S. Appl. No. 10/583,669 (US 2007/0154551).
Office Action issued on Aug. 17, 2010 by the Examiner in U.S. Appl. No. 10/583,669 (US 2007/0154551).
Office Action issued on May 3, 2011 by the Examiner in U.S. Appl. No. 10/583,669 (US 2007/0154551).
Office Action issued on Nov. 4, 2011 by the Examiner in U.S. Appl. No. 10/583,669 (US 2007/0154551).
Office Action issued on Feb. 14, 2012 by the Examiner in U.S. Appl. No. 10/583,669 (US 2007/0154551).
Notice of Allowance issued on Jun. 12, 2012 by the Examiner in U.S. Appl. No. 10/583,669 (US 2007/0154551).
Japanese Office Action for corresponding JP Application No. 2006-505237 dated Jun. 9, 2009—English translation included.
Japanese Office Action for corresponding JP Application No. 2006-505237 dated Jan. 19, 2010—English translation included.
Claims from corresponding JP Application No. 2006-505237, Published Oct. 26, 2006.

* cited by examiner

HIGH DRUG LOAD MESALAZINE SACHET

FIELD OF THE INVENTION

The present invention concerns a pharmaceutical formulation comprising a high load of active drug.

In particular, it concerns a particulate pharmaceutical formulation comprising a high load (i.e. with high weight % active drug) of 5-aminosalicylic acid (5-ASA, mesalamine, mesalazine) for oral administration as well as a method for producing it and a sachet for the formulation.

The present writ claims priority from the Danish patent application PA 2003 00612, The European patent application EP 03388023, and the U.S. provisional patent application 60/464649.

TECHNICAL BACKGROUND

Oral pharmaceutical formulations comprising mesalazine are known, which are either tablets or granulate. The granulate may be packed in sachets. For the purposes of the present invention a "sachet" will refer to an envelope or bag for a granulate, while "granulate" refers to particles, granulate or spheronised particles.

Presently, tablets containing 250 or 500 mg mesalazine are known. Tablets of 250 mg typically weigh about 540 mg, i.e. they have a drug load of (250/540)% by weight=46% by weight. Tablets containing up to 84% by weight mesalazine have been described in the patent application WO 00/44353 with the title "Pharmazeutische Zusammensetzungen".

For sachets, Dr. Falk Pharma has launched a product which claims to contain 500 mg mesalazine in a 930 mg sachet, corresponding to a drug load of 54% by weight.

Presently up to 4 g of mesalazine are often prescribed for the daily treatment of intestinal bowel diseases, such as Crohn's disease and Ulcerative Colitis.

If 4 g of mesalazine is administered in 250 mg tablets, the patient needs to swallow 16 tablets a day. Alternatively, 500 mg tablets may be administered, but with a drug load in the 50% range, the tablets will weigh about 1 g each, which many patients find rather large to swallow.

There exists a need to provide a product which allows administering large daily doses of drug without adversely affecting patient compliance.

Methods for manufacturing oral pharmaceutical formulations comprising mesalazine on an industrial scale are known. However, known methods of manufacture necessitate a high number of production steps to achieve a product having desirable release characteristics. This leads to cumbersome and expensive manufacture.

DISCLOSURE OF THE INVENTION

These problems and others mentioned below are addressed by aspects of the invention.

According to an aspect, the present invention concerns an oral pharmaceutical formulation, preferably for a sachet, comprising an amount of mesalazine selected among the group consisting of 55; 60; 65; 70; 75; 80; 85; 90; 92; 94 and 96% by weight. According to a preferred aspect, the formulation comprises 92-98, preferably 94-96,% by weight mesalazine.

These aspects provide a high load pharmaceutical composition.

For the purposes of the present invention "mesalazine" also encompasses pharmaceutically acceptable salts and esters thereof, such as those mentioned in WO 97/23199 p. 15, 1. 17-p. 6, 1. 12, as well as prodrugs, such as balsalazide.

The formulation is preferably in the form of a particulate material, e.g. granulate, spheres, pellets, particles, preferably granulate.

According to an aspect, the present invention concerns a pharmaceutical formulation further comprising a pharmaceutically acceptable binder, preferably Povidone, in an amount selected among the group consisting of 1; 2; 3; 4; 5; 6; 7; 8; 9; 10; and 12% by weight. According to a preferred aspect, the formulation comprises 1-10, preferably 2-8; more preferred 3-7; preferably 4-6; most preferred 5% by weight Povidone.

The pharmaceutically acceptable binder may comprise any acceptable binder such as Acacia, Gelatin, Hydroxypropyl cellulose, Hydroxypropylmethyl cellulose, Methylcellulose, Polyetylene glycol (PEG), Povidone, Sucrose, Starch or a mixture of any of these. Povidone (Polyvinylpyrrolidone, PVP) is preferred.

According to an aspect, the present invention concerns a pharmaceutical formulation further comprising a coating.

The coating should preferably comprise a release modifying agent, such as ethylcellulose, carnauba wax, shellac or a mixture of any of these. Ethylcellulose is preferred.

The selected coating depends inter alia on the desired release pattern. It may be chosen from rate limiting barrier materials, e.g. enteric or delayed coating material, such as polymethacrylate, commercially available in the form of Eudragits, e.g. Eudragit NE 40 D or Eudragit L 100. When a semi-permeable polymer is used, ethyl cellulose is the most preferred coating.

According to an aspect, the formulation is a modified release formulation, preferably an extended release formulation.

According to an aspect, the formulation comprises a coating, the ratio of the weight of said coating to the weight of said mesalazine or said pharmaceutically acceptable salt being selected among 0.1-10%; 0.3-7%; 0.5-5%; 0.7-3%; 0.8-2%; and 0.9-1.5%. The amount of coating may be adjusted to reach the desired release profile. Very high amount of coating may impede the release of active ingredient.

According to an aspect, the present invention concerns a pharmaceutical formulation essentially consisting of mesalazine, a pharmaceutically acceptable binder and a coating.

According to an aspect, the present invention concerns a pharmaceutical formulation having in vitro release characteristics of mesalazine of at least 40, 50, 60, 70, 80, or 90% released after 240 min, of the total amount of mesalazine in the formulation, measured in a model system using a USP Paddle System 2 operated at 37° C. with stirring at 100 rpm. Usually a higher release is preferred in order to ensure effective release in the intestines.

According to an aspect, the present invention concerns a pharmaceutical formulation having in vitro release characteristics of mesalazine of a) 5-25% released after 15 min;
b) 30-70%, preferably 40-60%, released after 90 min; and
c) 75-100% released after 240 min;

of the total amount of mesalazine in the formulation, measured in a model system using a USP Paddle System 2 operated at 37° C. with stirring at 100 rpm.

The dissolution parameters for the model system were: Dissolution medium: 1000 ml deaerated 0.1 M sodium phosphate buffer pH 7.5.

Apparatus: USP 23 Paddle method (Apparatus 2)

Shaft rotation speed: 100 rpm. 1 g sachets were used for experiments.

According to a first preferred aspect, the present invention concerns a pharmaceutical formulation having a similarity factor $f_2$ above a number selected from 25, 30, 35, 40, 45, 50, 55, 60, 65, and 70, as compared to a standard having the in vitro release characteristics of mesalazine of
 a) 12% released after 15 min;
 b) 50% released after 90 min; and
 c) 85% released after 240 min;
as measured under the conditions listed above.

The similarity factor $f_2$ is defined as $$f_2 = 50\log\left\{\left[1 + (1/n)\sum_{t=1}^{n}(R_t - T_t)^2\right]^{-0.5} * 100\right\}$$

wherein n is the number of time points, R(t) is the mean percent active ingredient dissolved of the standard, and T(t) is mean percent active ingredient dissolved of the formulation according to the invention. The similarity factor is usually considered satisfactory if in the range 50-100, but may for the purposes of the present invention be even smaller.

According to a second preferred aspect, the present invention concerns a pharmaceutical formulation having a similarity factor $f_2$ above a number selected from 25, 30, 35, 40, 45, 50, 55, 60, 65, and 70, as compared to a standard having the in vitro release characteristics of mesalazine of
 d) 21% released after 15 min;
 e) 68% released after 90 min; and
 f) 94% released after 240 min;
as measured under the conditions listed above.

According to an aspect, the present invention concerns a pharmaceutical formulation, wherein said pharmaceutical formulation is packed in a sachet.

According to an aspect, the present invention concerns a method for manufacturing a granulate comprising the steps:
 a) mixing mesalazine with granulation liquid;
 b) obtaining granulate by granulating, compacting or extruding;
 c) drying the granulate;
 d) adjusting the size of the granulate as necessary; and
 e) sieving the granulate as necessary;
characterised in the additional step of:
 f) coating the granulate;
and optionally further:
 g) sieving the coated granulate;
 h) air purging the coated granulate.

According to an aspect, the present invention concerns a method, wherein the coated granulate are packed in sachets.

Other suitable package forms are containers usually used for oral formulations.

This method provides a simple manufacturing method for pharmaceutical formulations.

According to an aspect of the invention a pharmaceutical composition is provided being produced without spheronization. The composition is thus obtainable without spheronization. Thereby the need for a spheronization aid is eliminated, allowing the pharmaceutical composition to have a high drug load.

Spheronization has been used to obtain a reproducible product on an industrial scale, the product being visually appealing and easy to administer, leading to high patient compliance.

It has until the present invention been considered neccessary to spheronise mesalazine drugs in order to obtain a visually appealing and easily administrable sachet product. Spheronisation implies the use of a spheronization aid or enhancer, such as microcrystalline cellulose. The presence of a spheronization aid leads to drug loads lower than obtainable with the present invention.

There exists a demand for a dust-free high load pharmaceutical composition. A pharmaceutical formulation meeting these criteria is achieved according to an aspect of the invention without spheronization. Such composition may be provided by obtaining a granulate. A granulate may be obtained by granulating, compacting or extruding, in order to achieve a product which is visually appealing to a person to whom said pharmaceutical formulation is administered. Compacting may be performed e.g. by roll compacting. The granulate is preferably obtained by extruding.

According to a certain preferred aspect of the present invention, the pharmaceutical composition is obtained according to co-pending patent application PCT/DK01/00677 with the title "Method for the preparation of a pharmaceutical composition comprising 5-aminosalicylic acid for use in treatment of Ulcerative Colitis and Crohn's Disease", with modifications. The modifications comprise that the coating should be adapted according to the present invention, and that after coating, sieving and nitrogen purging, the obtained granulate are packed in sachets, without the need for further excipients (cf. Example 3 and FIG. 4 of said application). It is especially preferred that the granulation liquid comprises at least 50%, more preferred 60%, preferably 70%, more preferred 80%, preferably 85%, more preferred 90%, w/w water.

According to an aspect, the present invention concerns the method, wherein the granulation liquid consists of Povidone dissolved in water.

According to an aspect, the present invention concerns the method, wherein said drying step c) is performed in a fluid bed dryer.

According to an aspect, the present invention concerns the method, wherein said adjusting of size step d) is performed by milling.

According to an aspect, the present invention concerns the method, wherein the sieving step e) is performed by selecting granulate passing a 1.8 mm sieve, but not passing a 0.5 mm sieve.

Other suitable sieves may be used, e.g. having sizes selected among the group consisting of 4.0; 3.15; 2.5; 2.0; 1.8; 1.6; 1.4; 1.25; 1.18; 1.0; 0.9; 0.8; 0.71; 0.6; 0.5 and 0.4 mm for selecting desired granulate. The sieves may be chosen to determine upper and/or lower limits of particle sizes.

According to another aspect, the resulting granules, after being milled, have a particle size distribution measured by sieve analysis where the main fraction is from 850 µm to 1000 µm. The holes in an extruder may be varied in order to obtain the desired particle size. According to an aspect, more than 75%, preferably more than 85% and most preferably more than 90% of the granules have a particle size from 850 µm to 1000 µm.

According to an aspect, the present invention concerns the method, wherein the coating step f) is performed with ethylcellulose.

According to an aspect, the present invention concerns the method, wherein the coating step f) is performed by spraying with an amount of coating material, adjusted according to the specific surface area, to be in the range 0.09-0.17 mg/cm$^2$, preferably 0.11-0.15 mg/cm$^2$, more preferred 0.12-0.14 mg/cm$^2$, followed by drying. These amounts have been found suitable for coating with ethylcellulose.

It has been discovered that the desired release profile may be obtained by adjusting the amount of coating material used according to the specific surface area.

The specific surface area may be measured by permeametry according to "Evaluation of a permeametry technique for surface area measurement of coarse particulate materials, International Journal of Pharmaceutics, Eriksson et al., 1990, 63, p. 189-199".

Granulate obtained according to co-pending patent application PCT/DK01/00677, preferably with modifications according to the present invention, is especially preferred, as is has a smooth surface facilitating measurement of specific surface area as well as subsequent coating.

In order to be able to determine the amount of coating that has to be applied to the granules the surface area is measured. Based on the measured correlation between the amount of coating per surface area and the dissolution rate profile, the amount of coating needed can be predicted from the measured surface area of the granules. The amount is adjusted by trial and error, as it depends on the exact conditions used, e.g. apparatus and excipients.

According to an aspect, the present invention concerns the method, wherein the sieving step g) is performed on a rotation sieve, preferably with a mesh size of 2.5 mm, in order to obtain coated granulate of a size smaller than or equal to 2.5 mm.

Other suitable sieves may be used, e.g. having sizes selected among the group consisting of 4.0; 3.15; 2.5; 2.0; 1.8; 1.6; 1.4; 1.25; 1.18; 1.0; 0.9; 0.8; 0.71; 0.6; 0.5 and 0.4 mm for selecting desired size of coated granulate.

According to an aspect, the present invention concerns a pharmaceutical formulation, preferably according to any of the aspects mentioned above, obtainable according to the method.

According to an aspect, the invention concerns pharmaceutical formulations for medical use.

According to an aspect, the present invention concerns the use of mesalazine for the manufacture of a pharmaceutical formulation according to the invention, comprising a total amount of mesalazine chosen among the group consisting of 0.5 g; 1.0 g; 1.5 g; 2 g; 3 g; 4 g; 5 g; 6 g; 8 g; and 10 g.

According to an aspect, the present invention concerns the use, wherein the medicament is for the treatment of intestinal bowel disease (IBD), preferably Crohns's Disease or Ulcerative Colitis.

The formulations according to the invention are suitable for the treatment of IBD.

According to an aspect the invention concerns a method for treatment of IBD, wherein the formulation according to the invention is administered to the patient, preferably 1, 2, 3 or 4 times daily.

The formulations according to the invention may be packed in different containers which allow administering to patients, such as capsules, blister packages, dispensers, glass or plastic containers, and sachets.

According to an aspect, the present invention concerns a sachet for a pharmaceutical formulation, preferably according to the invention.

The present sachet may be used for any pharmaceutical formulation, but is especially suitable for storing pharmaceuticals comprising sensitive compounds such as mesalazine.

According to an aspect, the present invention concerns a sachet, comprising the layers:

i) paper;
ii) bonding layer, preferably an adhesive such as polyethylene;
iii) barrier layer, preferably aluminium foil; and
iv) sealing layer, preferably low density polyethylene.

Mesalazine is sensitive to humidity, atmospheric air and/or light. A sachet for a product containing mesalazine should therefore preferably provide a barrier to humidity, atmospheric air and light. The sachet should also be easy to open for a patient, preferably without the use of additional tools, such as scissors. It has been a problem to provide a sachet with the necessary barrier properties without sacrificing the possibility of tearing open the sachet with human fingers. Further, existing sachets tend to suffer from the build up of static electricity. Preferably, a sachet should be easy to manufacture, easy to fill, easy to empty, and have an appealing look to improve patient compliance.

This aspect provides a sachet giving long storage stability for a pharmaceutical composition contained therein, e.g. where the active pharmaceutical ingredient is mesalazine. Further, the sachet is easy to tear and static electricity is eliminated, providing for a sachet which may be emptied completely for its contents. The combination of the sachet and the oral formulation according to the present invention provides for little build up of static electricity.

According to an aspect, the present invention concerns the sachet, wherein the bonding layer ii) preferably has a weight per unit area of 6-20 g/m$^2$, preferably 9-15 g/m$^2$, more preferred 12 g/m$^2$; the barrier layer iii) preferably has a thickness of 6-30 μm, more preferred 7-25 μm, preferably 9-25 μm, more preferred 8-20 μm, preferably 9-15 μm, more preferred 12 μm; and/or the sealing layer iv) preferably has a weight per unit area of 10-100 g/m$^2$, more preferred 15-75 g/m$^2$, preferably 20-50 g/m$^2$, more preferably 30-40 g/m$^2$, most preferred 35 g/m$^2$.

The outer paper i) has in a preferred embodiment a weight per unit area of 10-100 g/m$^2$, preferably 30-70 g/m$^2$, most preferred 50 g/m$^2$.

According to an aspect, the present invention concerns the use of the sachet for a pharmaceutical composition according to the invention.

The sachet has proven suitable for storing the pharmaceutical compositions according to the invention.

According to an aspect, the present invention concerns the use of the sachet for medical purposes.

According to an aspect of the present invention it is not limited to the use of mesalazine as the active ingredient, but also relates to other active ingredients, such as the ingredients mentioned in WO 00/44353, p. 12-16. Other low potent active ingredients are suitable for the present invention. Especially ibuprofen is envisioned as replacing mesalazine.

According to an aspect of the present invention further excipients may be comprised in the composition according to the invention, such as fillers, disintegrants, pH adjusters, or surfactants. Such excipients are well known from the literature, see e.g. WO 00/44353, p. 16-20, for a number of suitable excipients.

EXAMPLES

Unless otherwise stated, all percentages are in % by weight.

Example 1

A batch for the production of 180,000 sachets of prolonged release granules was provided as follows.

| Constituents | Quantity | Specification |
| --- | --- | --- |
| Mesalazine | 180 kg | Ferring |
| Povidone | 9 kg | Ph. Eur. |
| Water, purified | 33.3 kg** | Ph. Eur. |
| Ethylcellulose | 1.9 kg*** | Ph. Eur. |
| Acetone | 188 kg** | Ph. Eur. |

**Evaporates during production.
***The amount of ethylcellulose was adjusted to ensure the desired dissolution profile of the finished product.
Ph. Eur. refers to the current edition at the time of filing of the present application.

The manufacturing method follows closely the manufacturing method described in co-pending patent application PCT/DK01/00677, with some exceptions. The amount and type of ingredients is adjusted, and in particular the amount of ethylcellulose is reduced to obtain the desired dissolution profile. In this example no tablets were made, so excipients for this purpose are not included, no dry blending is performed after the air purging, and no tableting performed. The granulate product resulting from the present process is therefore different from the tablet of said application.

The manufacturing process for the formulation can be divided into 9 steps:
1. Preparation of granulation liquid
2. Granulation of Mesalazine with water and PVP
3. Extrusion
4. Fluid bed drying
5. Milling
6. Sieving
7. Coating
8. Sieving
9. Air purging

| Equipment for the production | Function |
| --- | --- |
| NICA Extruder E220 | Extrusion |
| Rotostat T05 | Blending |
| NIRO Fluid bed dryer | Drying |
| Quadro Comil U10 | Milling |
| Mogensen sieve | Sieving |
| Huttlin Kugelcoater HKC 400 | Coating |
| Prodima rotation sieve | Sieving |
| Purging unit | Air purge |

Step 1:
For one batch of granulation liquid water is filled into a Müller drum. The mixer is put into position and started. Polyvinylpyrrolidone (PVP) is slowly sprinkled onto the water and the mixer is allowed to run a fixed time until all PVP is dissolved.

Step 2 and 3:
Mesalazine is placed in a vibrating Prodima hopper and by the use of a conveyor the mesalazine is transported up to a weight belt feeder dosing the mesalazine into the continuous Niro line. In the first part of the Niro line the mesalazine and the water solution of PVP are mixed to a wet mass before being transported into the extruder. After extrusion of the wet mass of mesalazine and PVP/water through a screen mesh 0.9 mm, the granules fall directly into the fluid bed dryer.

Step 4:
The fluid bed dryer is divided into two main sections. In the first section, the granules are dried on the surface to prevent them from sticking together. In this section of the fluid bed, a random mixing of the granules takes place. After a certain residence time, the granules are moved into the second part of the dryer where the actual drying takes place. In the second part of the dryer the granules are guided by the use of the drying air through the dryer (special pattern of holes in the gill plate). When the granules are dry they are allowed to fall into a drum placed under the fluid bed. The fluid bed is constructed in such a way that the overall dwelling time in the fluid bed is approximately 2½% hours.

Step 5:
The drums containing the dry granules are placed upside down on top of the mill and the granules are gently milled using a screen, which will only break the granules that are too long. After passing the mill, the granules are allowed to fall into a drum.

Step 6:
Due to the fact that the milling process generates a small amount of undersized granules, the granules are sieved using a Mogensen vibration sieve. Granules, which pass the screen 0.8 mm, are discarded or can be collected for reprocessing stored in airtight, labelled containers.

Step 7:
200 kg of sieved granules are coated in a Kugel coater (fluid bed system) with a coating liquid consisting of ethyl cellulose dissolved in acetone.

In order to be able to determine the right amount of ethylcellulose necessary to apply on the granules to get the desirable dissolution rate profile, the surface area of the granules is measured prior to the coating process. The prediction of the quantity of coating that is necessary to apply on the granules has been developed based on the fact that there is a correlation between the amount of coating per surface area and the dissolution rate of the granules.

When the coating step was performed in a HKC 400 Hüttlin Kugel coater and followed by production scale sieving, release characteristics according to the invention, as measured as released % of total amount of mesalazine or according to the first preferred aspect as defined by the similarity factor, was achieved when the amount of ethylcellulose was adjusted to 0.13 mg/cm$^2$.

After finishing the coating process, the coated granules are loaded into a drum for further processing.

Step 8:
After the coating process, the coated granules are sieved in a Prodima rotation sieve. Large lumps are discarded.

Step 9:
After sieving the batch of coated granules, they are divided into two drums for purging with compressed air or nitrogen. The granules are purged for 6-14 hours. This purging process is necessary to reduce the amount of residual solvent (acetone) in the coated granules.

This batch gave granulate with the following approximate composition:

| | |
| --- | --- |
| mesalazine | 94.3% |
| Povidone | 4.7% |
| Ethylcellulose | 1.0% |

The granulate was subsequently filled into sachets.
The material of the sachets had the following composition:

| | |
| --- | --- |
| Paper, claycoated | 50 g/m$^2$ |
| Polyethylene, low density | 12 g/m$^2$ |
| Aluminium foil | 12 µm |
| Polyethylene, low density | 35 g/m$^2$ |

For the present example 12 g/m$^2$ PE corresponds to 13 µm, and 35 g/m$^2$ PE corresponds to 38 µm. The material had a grammage of 129 g/m². The permeability to water vapour was <0.05 g/m², 24 h, 25° C., 75% RH, and to $O_2$<0.05 ml/m², 24 h, atm, 23° C., 75% RH.

The sachets were folded around the filling tube of a filling/sealing station, such that the paper was on the outside of the sachet, and then sealed lengthwise, with a low density polyethylene as a sealing layer. After forming the cross seal at the bottom the sachet is filled with granulates, and then sealed again at the top and finally cut.

All citations are incorporated in their entirety by reference.

The invention claimed is:

1. A pharmaceutical formulation suitable for oral administration and in the form of coated, flowable granules comprising:
    92 to 98% by weight of mesalazine or a pharmaceutically acceptable salt thereof;
    2 to 8% by weight of polyvinylpyrrolidone; and
    a coating comprising ethylcellulose, the ratio of the weight of the coating to the weight of the mesalazine or pharmaceutically acceptable salt thereof being 0.7-3%;
    the coated, flowable granules being in a sachet, capsule or blister package;
    wherein the coated granules, when suspended in an aqueous buffer at pH 7.5, release the mesalazine according to a release profile in which:
    a) 5-25% of the total amount of mesalazine or pharmaceutically acceptable salt thereof in the granules is released after 15 min;
    b) 30-70% of the total amount of mesalazine or pharmaceutically acceptable salt thereof in the granules is released after 90 min; and
    c) 75-100% of the total amount of mesalazine or pharmaceutically acceptable salt thereof in the granules is released after 240 min;
    when measured in a model system using a USP Paddle System 2 operated at 37° C. with stirring at 100 rpm.

2. The formulation of claim 1, comprising 4 to 6% by weight of polyvinylpyrrolidone.

3. The pharmaceutical formulation of claim 1, having a similarity factor f2 above 30 as compared to a standard formulation having in vitro release characteristics such that
    a) 12% of the total amount of mesalazine in the standard formulation is released after 15 min;
    b) 50% of the total amount of mesalazine in the standard formulation is released after 90 min; and
    c) 85% of the total amount of mesalazine in the standard formulation is released after 240 min;
    when measured in a model system using a USP Paddle System 2 operated at 37° C. with stirring at 100 rpm.

4. The pharmaceutical formulation of claim 3, having a similarity factor f2 above 40 as compared to the standard formulation.

5. The pharmaceutical formulation of claim 3, having a similarity factor f2 above 50 as compared to the standard formulation.

6. The pharmaceutical formulation of claim 1, consisting of mesalazine, polyvinylpyrrolidone, and coating.

7. The pharmaceutical formulation of claim 1, provided in a sachet comprising a total dosage amount of mesalazine or a pharmaceutically acceptable salt thereof selected from the group consisting of 0.5 g, 1.0 g., 1.5 g., 2 g, 3 g, 4 g, 5 g, 6 g, 8 g, and 10 g.

8. The pharmaceutical formulation of claim 1, having in vitro release characteristics such that 40-60% of the total amount of mesalazine or pharmaceutically acceptable salt thereof in the formulation is released after 90 min, when measured in a model system using a USP Paddle System 2 operated at 37° C. with stirring at 100 rpm.

* * * * *